United States Patent
Link

[11] Patent Number: 5,944,759
[45] Date of Patent: Aug. 31, 1999

[54] JOINT ENDOPROSTHESIS

[75] Inventor: Helmut D. Link, Hamburg, Germany

[73] Assignee: Waldemar Link (GmbH & Co), Germany

[21] Appl. No.: 08/926,952

[22] Filed: Sep. 10, 1997

[30] Foreign Application Priority Data

Sep. 12, 1996 [DE] Germany ............ 296 15 920 U

[51] Int. Cl.$^6$ ............................................. A61F 2/38
[52] U.S. Cl. ............................................. 623/20
[58] Field of Search ................................ 623/20

[56] References Cited

U.S. PATENT DOCUMENTS

| | | | |
|---|---|---|---|
| 3,728,742 | 4/1973 | Averill | 623/20 |
| 4,034,418 | 7/1977 | Jackson | 623/20 |
| 4,055,862 | 11/1977 | Farling | 623/20 |
| 4,085,466 | 4/1978 | Goodfellow et al. | 3/1.91 |
| 4,166,292 | 9/1979 | Bokros | 3/1.91 |
| 4,207,627 | 6/1980 | Cloutier | 3/1.911 |
| 4,479,271 | 10/1984 | Bolesky et al. | 3/1.911 |
| 4,997,445 | 3/1991 | Hodorek | 623/16 |
| 5,080,675 | 1/1992 | Lawes | 623/20 |
| 5,176,710 | 1/1993 | Hahn | 623/20 |
| 5,236,462 | 8/1993 | Mikhail | 623/20 |

FOREIGN PATENT DOCUMENTS

| | | | |
|---|---|---|---|
| 681845 | 11/1995 | European Pat. Off. | A61L 27/00 |
| 2743716 | 7/1997 | France | A61F 2/38 |
| 227338 | 10/1910 | Germany . | |
| 1964781 | 6/1972 | Germany . | |
| 3838568 | 5/1990 | Germany | A61F 2/30 |
| 4006714 | 9/1990 | Germany | A61F 2/30 |

Primary Examiner—Michael J. Milano
Attorney, Agent, or Firm—Medlen & Carroll, LLP

[57] ABSTRACT

Joint endoprosthesis with a prosthesis part which on one side forms a slide surface (1), on the other side is to be connected to the bone without any bend-resistant intermediate spacer, and is made of a polymer material which favors sliding, such as polyethylene. The prosthesis part has a centrally situated area (3) in which it is mainly exposed to the loading and wear. The prosthesis part is essentially plate-shaped. It contains a reinforcement element which exhibits tensile strength, surrounds the main area of loading and wear and lies at least partially within the third of the thickness remote from the slide surface.

9 Claims, 1 Drawing Sheet

JOINT ENDOPROSTHESIS

This application claims priority benefit of German Patent Application Serial Number 296 15 920.4 filed Sep. 12, 1996.

FIELD OF THE INVENTION

The invention relates to a joint endoprosthesis with a prosthesis part which on one side forms a slide surface, on the other side is to be connected to the bone without any bend-resistant intermediate spacer, and is made of a polymer material which favors sliding, such as polyethylene.

BACKGROUND OF THE INVENTION

Polymer material favoring sliding, such as high-density polyethylene, has a low modulus of elasticity and therefore tends to bend under local loading. It is therefore generally implanted using a bend-resistant, and in most cases metal, support plate on which the plateau lies via its entire lower surface (U.S. Pat. No. 4,997,445, U.S. Pat. No. 5,236,462, U.S. Pat. No. 4,207,627) or is connected to another stiff plate (EP-A 68 18 45). If it is fitted without using such a rigid support (DE-B 19 64 781), its thickness must be undesirably large. These principles are already applicable if the plateau or its support plate is connected to the bone by bone cement. They are all the more applicable in cases of cementless implantation in which a relative movement between the surface of the implant and the bone has to be avoided. With a view to simplifying the prosthesis structure and to reducing the structural height to be provided for the plateau together with its support, it would be desirable to obtain a plateau which, despite the low modulus of elasticity of polymer materials favoring sliding, has a high degree of flexural strength. It is known (DD-A 227 328) to strengthen a tibial plateau by means of the isotropic incorporation of compacting fibers into the polyethylene material. Since these reduce the homogeneity of the material in the slide surface and thus adversely affect the slide and wear properties, this measure has not proven effective. This also applies to the layered build-up of a plateau from oriented polymer fibers (DE-A 40 06 714). Attempts have therefore been made to embed a reinforcement layer into an acetabular socket (DE-A 38 38 568) at a distance from the slide surface corresponding to the maximum thickness of wear which is to be expected in practice, with the result that the total thickness of the implant increases accordingly.

Knee prostheses are also known in which the joint surface is formed from a nonrigid material without inherent flexural strength; in this case a bend-resistant base is imperative (U.S. Pat. No. 4,085,466). To ensure that the nonrigid material does not lose its shape under loading, it is delimited by a ring exhibiting tensile strength. Such a ring with tensile strength is also necessary if. pyrolytic carbon is used as the material (U.S. Pat. No. 4,166,292), as this is sensitive to tensile stresses which may occur if the prosthesis part is not prevented by a surrounding ring, which is practically rigid as a result of a high modulus of elasticity, from laterally expanding under axial loading. In neither of these two cases is the flexural strength of the implant increased by being enclosed in a ring.

SUMMARY OF THE INVENTION

The invention is based on the object of making available a prosthesis part, as has been described hereinabove with reference to DE-A 38 38 568, which permits a smaller implant thickness. The solution according to the invention lies in the fact that the prosthesis part is plate-shaped and the reinforcement element is arranged essentially outside the main area of loading and surrounds the latter.

The invention is based on the recognition that to reduce the tendency of the implant to bend, it is not strictly necessary to provide the reinforcement directly beneath the site of loading. If the reinforcement surrounds the latter, with tensile strength, in a layer remote from the slide surface, and is closely adjacent to it, the total bending of the implant is greatly reduced. As will be readily appreciated, the outer part of the implant provided with the reinforcement element can scarcely yield to the bending stress. It therefore acts in a flexurally rigid manner. As the central area, not provided directly with a reinforcement element, is as it were clamped inside the outer, reinforced area, its bending ability too is reduced. For a given thickness, the total deformation of the implant under a given load is at any rate considerably smaller than in previously disclosed, non-reinforced implants. Compared with known implants which contain a reinforcement layer, the thickness can be significantly reduced because, in the central area of loading exposed to wear, there is a wear distance which is not reduced by the reinforcement element. The invention thus leads to the advantage that it is possible to make available implants which combine comparatively high flexural resistance and small thickness.

The feature which states that the reinforcement element is embedded in the implant is intended to signify that it does not simply encircle the latter around the sides. Thus, it can be arranged nearer the central area exposed to loading and wear, so that its action increasing the flexural rigidity can develop near this area. The reinforcement element is preferably surrounded on all sides by the remaining implant material; this is not strictly necessary, however, if a sufficiently shear-resistant connection between the reinforcement element and the remaining implant material can be obtained without such a surround.

It is important that it counteracts the radial expansion of the lower layer of the plateau subjected to expansion during bending. For this reason it will often be expedient to arrange the reinforcement element exclusively in the lower half or even in the lower third or lower quarter of the thickness of the plateau. The expression "lower" means: distant from the slide surface.

To be able to enclose the main area of loading, the reinforcement is preferably of an annular design. An annular shape creates the optimum geometric conditions for the take-up of force, but is not necessary. For example, an ovoid or D-shaped configuration is generally adequate.

The feature which states that the implant should be plate-shaped means that the reinforcement element can be located in the same plane in which tensile stresses can develop within the main area of loading. In the case of a hollow spherical implant, such as an acetabular socket for example, this condition is not satisfied, because an expansion deformation, in the main area of loading, of that layer of the implant remote from the slide surface cannot essentially be prevented by a reinforcement situated further outside and lying in another plane. The main area of application of the invention therefore concerns tibial plateaus of knee joint prostheses. For the configuration of the implant on its slide surface side, the expression "plate-shaped" does not apply.

The invention is explained in greater detail below, with reference being made to the drawing which depicts advantageous illustrative embodiments in a diagrammatic manner.

DETAILED DESCRIPTION OF THE INVENTION

Figure 1:
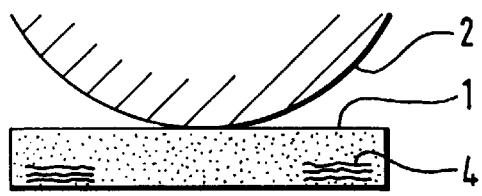
FIG. 1 shows a diagrammatic representation of a tibial plateau with the associated femoral slide surface in sagittal section.
Figure 2:
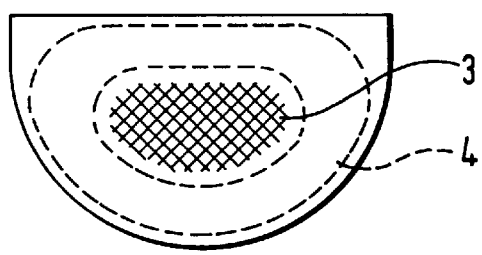
FIG. 2 shows a plan view of the tibial plateau according to FIG. 1, and FIGS. 3 to 6 show sagittal sections through alternative embodiments of the tibial plateau.
Figure 3:

In the example in FIG. 1, the plateau is a flat plate with a plane upper slide surface 1 and with an approximately semicircular contour, which plate interacts with a curved femoral slide surface 2. The upper slide surface 1 of the plateau can also be troughed, as is indicated in FIG. 3, as far as partial congruence of the slide surfaces 1 and 2. In general, however, the plateau-side slide surface 1 will be flat or have an essentially greater radius of curvature than the slide surface 2 interacting with it. The result of this is that the stressing of the plateau takes place mainly within a limited area which was referred to above as the main area of loading or main area of wear and which in FIG. 2 is indicated by crosshatching, by way of example. The point at which the opposite slide surface 2 touches the slide surface 1 of the plateau can lie at different locations within the main area of loading 3, depending on the individual requirements and the arbitrary relative positioning of the joint components in relation to one another. In constructing the prosthesis, the main area of loading is regarded as that area in which, statistically, the loading mostly occurs.

Because of this greater loading of the plateau in places, the latter is exposed to a bending stress which is greater, the more flexible the supporting surface is, which supporting surface is formed by the natural bone tissue, which in many cases, after resection, has a spongy structure under the plateau center and is therefore comparatively flexible. This is true not only in the case of cementless implantation, but also in the case of the anchoring of the plateau by means of cement. In the lower part of the plateau, near the loading position, this bending stress leads to a tensile stress which has the effect of expanding the plateau in the lower part. Depending on the flow properties of the material, this expansion can also lead to permanent deformation unless appropriate precautions are taken. According to the invention, these precautions consist of a reinforcement element 4 which is arranged in an annular fashion principally in the lower area of the plateau and which closely surrounds the main area of loading 3. It has tensile strength in the circumferential direction and has a higher modulus of elasticity than the other plateau material, indicated by stippling in the cross section, and thereby counteracts the expansion which is to be expected because of the bending stress of the plateau part in its lower part. It cannot completely prevent this expansion. But this is not necessary either, as long as the expansion is limited to such a low extent that the flexible bone tissue located underneath can follow the expansion movement and thus no relative movement, or no substantial relative movement, can take place between the lower surface of the plateau and the bone tissue.

By virtue of the fact that the reinforcement element leaves the main area of loading free, an unreduced reserve for wear is available there. The presence of the reinforcement element in the plateau does not therefore necessitate a greater thickness; instead, the thickness can be freely dimensioned in accordance with other considerations.

The cross-sectional shape of the reinforcement element in FIG. 1 is that of a flat plate, whereas FIG. 3 shows a cross-sectional configuration in which the thickness of the reinforcement element decreases toward the main area of loading 3 and its upper limit surface dips down. In this way the reinforcement element can be brought nearer to the main area of loading 3 or can even extend into the latter via its inner edge. An inward tapering of the reinforcement element can also be used for the purpose of giving the plateau different local flexibility in order to allow this flexibility to increase inward. The local flexibility of the implant can thus be adapted in the desired manner to that of the bone.

Figure 4:

This concept is taken further in FIG. 4, which shows an illustrative embodiment in which a thin layer 6 of the reinforcement element is guided through underneath the main area of loading 3, while, as was mentioned above, the main cross section of the reinforcement element is located annularly outside the main area of loading 3. This thin layer 6, which has practically no influence on the thickness of the plateau, has the main purpose of transferring the tensile stress occurring in the lower area of the plateau to the reinforcement element 4 located annularly outside the main area of loading 3.

Figure 5:

Whereas the illustrative embodiments in FIGS. 1 to 4 show the reinforcement element enclosed all around by the plateau material, in FIG. 5 it is assumed that the plateau material has a recess within an annular edge area, into which recess the reinforcement element is introduced with a shape fit and with resistance to shearing. The shearing resistance is indicated in the drawing by the fact that the interacting surfaces 5 of the recess and of the reinforcement element are designed engaging in one another via a surface roughness, for example with circular ribs and grooves. In this case, the reinforcement element can be a part which is separable from the plateau. However, a permanent connection is preferred whose shearing resistance is provided not by the surface roughness, or not only by the surface roughness, but also by an adhesive bonding. For example, the reinforcement element can be formed by a fiber strand which is saturated with a suitable and initially ductile synthetic and is pressed into the recess until hardened, the synthetic resin undergoing a chemical or physical bonding with the surface of the plateau material and embedding itself in the surface roughness thereof. It can also be a metal ring.

Figure 6:

Finally, FIG. 6 shows an illustrative embodiment indicating diagrammatically that the reinforcement element is not only embedded in the plateau or intimately connected thereto, but also forms projections (loops, small hooks, porosity, etc.) which project below the lower surface of the plateau and are suitable for cemented or cementless connection to the bone.

In the other illustrative embodiments, we did not represent and discuss anchoring elements which provide for the connection between the plateau and the associated bone. It will be appreciated that such anchoring members are generally provided in the form of pins, projections, porous coating or the like.

The reinforcement element can consist of any material able to afford the desired tensile strength, for example fibers, filaments, wires, rings of polymer material or metal. These can be embedded directly in the plateau material or can be connected to it. In the case of fibers or filaments, they can also be provided with a synthetic resin impregnation and thus be joined to form a unified structure which is in turn connected to the material of the plateau. The reinforcement element is preferably flexible, but can also be rigid.

Where reference is made in the present context to a "lower" area of the plateau, this signifies the area remote from the slide surface 1.

I claim:

1. A joint endoprosthesis, comprising:
   a) a plate-shaped prosthesis part comprising a first side and a second side, said first side having a slide surface comprised of a material which favors sliding, said slide surface having a central region associated with loading and wear; said central region having a thickness defined by the distance between said slide surface and said second side, said second side of said prosthesis part adapted to be connected to bone without any bend-resistant intermediate spacer; and
   b) a reinforcement element having tensile strength, said reinforcement element positioned principally in the lower half of said plate-shaped prosthesis and outside said central region associated with loading and wear such that said central region is surrounded without adding thickness to said central region.

2. The joint endoprosthesis of claim 1, wherein said reinforcement element is embedded in said prosthesis part.

3. The joint endoprosthesis of claim 1, wherein said reinforcement element is annular in shape.

4. The joint endoprosthesis of claim 1, wherein said reinforcement element is ovoid in shape.

5. The joint endoprosthesis of claim 1, wherein said reinforcement element is D-shaped.

6. The joint endoprosthesis of claim 1, wherein said material which favors sliding comprises polyethylene.

7. The joint endoprosthesis of claim 1, wherein said slide surface is troughed.

8. A joint endoprosthesis system, comprising:
   a) a plate-shaped prosthesis part comprising a tibial plateau having a first side and a second side, said first side having a slide surface comprised of a material which favors sliding, said slide surface having a central region associated with loading and wear, said central region having a thickness defined by the distance between said slide surface and said second side, said second side of said prosthesis part connected to bone; and
   b) an annular shaped reinforcement element positioned principally in the lower half of said plateau such that it closely surrounds said central region without adding thickness to said central region, said reinforcement element comprised of material having a higher modulus of elasticity than the material of said plateau and providing tensile strength in the circumferential direction, and wherein said reinforcement element comprises an outer edge and an inner edge, and wherein the thickness of said outer edge is greater than the thickness of said inner edge.

9. A method, comprising;
   a) providing:
      i) a subject having a knee joint, and
      ii) a joint endoprosthesis, comprising:
         a) a plate-shaped prosthesis part comprising a first side and a second side, said first side having a slide surface comprised of a material which favors sliding, said slide surface having a central region associated with loading and wear, said central region having a thickness defined by the distance between said slide surface and said second side, said second side of said prosthesis part adapted to be connected to bone, and
         b) a reinforcement element having tensile strength, said reinforcement element attached to said prosthesis part principally in the lower half of said plate-shaped prosthesis such that said central region is surrounded without adding thickness to said central region, and wherein said reinforcement element is annular in shape and comprises a wire ring embedded in said prosthesis part, and
      iii) a bone attachment means, wherein said bone attachment means comprises bone cement;
   b) positioning said endoprosthesis in said knee joint of said subject such that said plate-shaped prosthesis part serves as a tibial plateau; and
   c) securing said second side of said prosthesis part of said endoprosthesis to bone with said bone attachment means.

* * * * *